US009968660B2

(12) United States Patent
Kamakura et al.

(10) Patent No.: US 9,968,660 B2
(45) Date of Patent: May 15, 2018

(54) METHOD OF BONE REGENERATION OR BONE AUGMENTATION

(71) Applicant: TOYOBO CO., LTD., Osaka-shi, Osaka (JP)

(72) Inventors: Shinji Kamakura, Sendai (JP); Satoru Nakajou, Sendai (JP); Atsushi Iwai, Otsu (JP); Fumihiko Kajii, Otsu (JP); Hidenori Tanaka, Otsu (JP)

(73) Assignee: TOYOBO CO., LTD., Osaka-shi (JP)

( * ) Notice: Subject to any disclaimer, the term of this patent is extended or adjusted under 35 U.S.C. 154(b) by 55 days.

(21) Appl. No.: 15/094,724

(22) Filed: Apr. 8, 2016

(65) Prior Publication Data
US 2017/0290891 A1    Oct. 12, 2017

(51) Int. Cl.
| A61K 38/29 | (2006.01) |
| A61P 5/18 | (2006.01) |
| C07K 14/635 | (2006.01) |
| A61K 9/00 | (2006.01) |
| A61L 31/04 | (2006.01) |
| A61L 31/12 | (2006.01) |
| A61L 31/14 | (2006.01) |

(52) U.S. Cl.
CPC ............ *A61K 38/29* (2013.01); *A61K 9/0014* (2013.01); *A61K 9/0019* (2013.01); *A61L 31/044* (2013.01); *A61L 31/123* (2013.01); *A61L 31/146* (2013.01); *A61L 2430/02* (2013.01)

(58) Field of Classification Search
None
See application file for complete search history.

(56) References Cited

U.S. PATENT DOCUMENTS

| 2008/0176787 A1* | 7/2008 | Morley ................ A61K 38/29 514/11.8 |
| 2008/0234396 A1 | 9/2008 | Shoji et al. |
| 2009/0005868 A1* | 1/2009 | Gundlapalli .......... A61F 2/4644 623/11.11 |
| 2009/0149634 A1 | 6/2009 | Shoji et al. |
| 2010/0129422 A1* | 5/2010 | Han ..................... A61L 27/18 424/426 |
| 2011/0009872 A1* | 1/2011 | Mistry ................. A61F 2/4603 606/99 |
| 2014/0170202 A1 | 6/2014 | Peters et al. |

FOREIGN PATENT DOCUMENTS

| JP | 5-70113 A | 3/1993 |
| JP | 2002-274968 A | 9/2002 |
| JP | 2003-260124 A | 9/2003 |
| JP | 2004-508133 A | 3/2004 |
| JP | 2005-279078 A | 10/2005 |
| JP | 2006-167445 A | 6/2006 |
| JP | 2009-132601 A | 6/2009 |
| JP | 2010-273847 A | 12/2010 |
| JP | 2012-41344 A | 3/2012 |
| JP | 2014-515966 A | 7/2014 |
| JP | 2014-528734 A | 10/2014 |
| WO | 02/022045 A1 | 3/2002 |
| WO | 2013/165333 A1 | 11/2013 |

OTHER PUBLICATIONS

Ji Yun et al., "Effect of systemic parathyroid hormone (1-34) and a beta-tricalcium phosphate biomaterial on local bone formation in a critical-size rat calvarial defect model", Journal of Clinical Periodontology, vol. 37, pp. 419-426, 2010.
Shinji Kamakura et al., "New scaffold for recombinant human bone morphogenetic protein-2", Journal of Biomedical Materials Research, 71A, pp. 299-307, 2004.
Shinji Kamakura et al., "The primary of octacalcium phosphate collagen composites in bone regeneration", Journal of Biomedical Materials Research, 83A, pp. 725-733, 2007.
Shinji Kamakura et al., "Dehydrothermal treatment of collagen influences on bone regeneration by octacalcium phosphate (OCP) collagen composites", Journal of Tissue Engineering and Regenerative Medicine, vol. 1, pp. 450-456, 2007.
Aritsune Matsui et al., "The Regenerated Bone Quality by Implantation of Octacalcium Phosphate Collagen Composites in a Canine Alveolar Cleft Model", The Cleft Palate-Craniofacial Jornal, vol. 51, No. 4, pp. 420-430, Jul. 2014.
Tadashi Kawai et al., "First Clinical Application of Octacalcium Phosphate Collagen Composite in Human Bone Defect" Tissue Engineering: Part A. vol. 20, Nos. 7 and 8, pp. 1336-1341, 2014.
Shinji Kamakura et al., "Octacalcium Phosphate Combined with Collagen Orthotopically Enhances Bone Regeneration", Journal of Biomedical Materials Research, 79B, pp. 210-217, 2006.
Sergey V. Dorozhkin, "Biphasic, triphasic and multiphasic calcium orthophosphates", Acta Biomaterialia, vol. 8, pp. 963-977, 2012.
"Bone Augmentation", Medical Dictionary for the Dental Professions, 2012 (1 page).
"Bone Augmentation", The Dental Impant Experts, American Academy of Implant Industry, 2013 (2 pages).
"Bone regeneration", Biology-Online Dictionary, 2005 (2 pages).
Masahiko Takahata et al., "Delayed Short-Course Treatment With Teriparatide (PTH 1-34) Improves Femoral Allograft Healing by Enhancing Intramembranous Bone Formation at the Graft-Host Junction", Journal of Bone and Mineral Research, vol. 27, No. 1, pp. 26-37, Jan. 2012.
Tadashi Kawai et al., "Synthetic Octacalcium Phosphate Augments Bone Regeneration Correlated with Its Content Collagen Scaffold" Tissue Engineering: Part A. vol. 15, No. 1, pp. 23-32, 2009.
Shinji Kamakura et al., "Implantation of octacalcium phosphate combined with transforming growth factor-beta1 enhances bone repair as well as resorption of the implant in rat skull defects", Journal of Biomedical Materials Research, vol. 57, pp. 175-182, 2001.
Bernard J. Costello, "Regenerative Medicine for Craniomaxillofacial Surgery", Oral Maxillofacial Surg Clin N Am 22, pp. 33-42, 2010.

(Continued)

*Primary Examiner* — Marcela M Cordero Garcia
(74) *Attorney, Agent, or Firm* — Westerman, Hattori, Daniels & Adrian, LLP

(57) ABSTRACT

The present invention provides a means effective for bone regeneration or bone augmentation.
Provided is a method of bone regeneration or bone augmentation, comprising:
  implanting a porous composite at a site in need of the bone regeneration or bone augmentation, and
  administering parathyroid hormone (PTH) to a subject in need of the bone regeneration or bone augmentation,
  wherein the porous composite comprises calcium phosphate.

19 Claims, 5 Drawing Sheets
(3 of 5 Drawing Sheet(s) Filed in Color)

(56) References Cited

OTHER PUBLICATIONS

"The Japanese Journal of Pediatric Dentistry", 2013, vol. 51, No. 3, pp. 333-339. Cited in the Japanese Office Action dated Sep. 27, 2016. (with English Abstract).

C. Tam, et al., "Parathyroid Hormone Stimulates the Bone Apposition Rate Independently of Its Resorptive Action: Differential Effects of Intermittent and Continuous Administration", Endocrinology, 1982, vol. 110, No. 2, pp. 506-512.

R. Jilka, et al., "Increased bone formation by prevention of osteoblast apoptosis with parathyroid hormone", The Journal of Clinical Investigation, Aug. 1999, vol. 104, No. 4, pp. 439-446.

H.L. Chan, et al., "Parathyroid Hormone Applications in the Craniofacial Skeleton", Journal of Dental Research, Oct. 15, 2012, vol. 92, No. 1, pp. 18-25.

M. Ali, et al., "Effects of intermittent parathyroid hormone treatment on new bone formation during distraction osteogenesis in rat mandible", Oral Surg Oral Med Oral Pathol Oral Radiol, Jul. 2012, vol. 114, No. 1, pp. e36-e42.

J. Jacobson, et al., " Teriparatide Therapy and Beta-Tricalcium Phosphate Enhance Scaffold Reconstruction of Mouse Femoral Defects," Tissue Engineering: Part A, 2011, vol. 17, No. 3 and 4, pp. 389-398.

T. Morimoto, et al., "Effect of Intermittent Administration of Teriparatide (Parathyroid Hormone 1-34) on Bone Morphogenetic Protein-Induced Bone Formation in a Rat Model of Spinal Fusion", J Bone Joint Surg Am., 2014, vol. 96, No. 13, pp. e107(1-8).

M. Pensak, et al., "Combination Therapy with PTH and DBM Cannot Heal a Critical Sized Murine Femoral Defect", Journal of Orthopaedic Research, 2015, vol. 33, pp. 1242-1249.

H. Rowshan, et al., "Effect of Intermittent Systemic Administration of Recombinant Parathyroid Hormone (1-34) on Mandibular Fracture Healing in Rats", J Oral Maxillofac Surg, 2010, vol. 68, pp. 260-267.

B.W. Stancoven, et al., "Effect of bone morphogenetic protein-2, demineralized bone matrix and systemic parathyroid hormone (1-34) on local bone formation in a rat calvaria critical-size defect model", Journal of Periodontal Research, 2012, pp. 1-9.

Y. Tanuma, et al., "Comparison of bone regeneration between octacalcium phosphate/collagen composite and β-tricalcium phosphate in canine calvarial defect", Oral Surg Oral Med Oral Pathol Oral Radiol, 2013, vol. 115, No. 1, pp. 9-17.

A. Watanabe, et al., "Osteosarcoma in Sprague-Dawley rats after long-term treatment with teriparatide (human parathyroid hormone (1-34))", The Journal of Toxicological Sciences, 2012, vol. 37, No. 3, pp. 617-629.

H. Kaneko, et al., "Proteome analysis of rat serum proteins adsorbed onto synthetic octacalcium phosphate crystals", Analytical Biochemistry, Jul. 26, 2011, vol. 418, pp. 276-285.

\* cited by examiner

METHOD OF BONE REGENERATION OR BONE AUGMENTATION

TECHNICAL FIELD

Disclosed is a combination of a calcium phosphate-containing porous composite and PTH, and the use thereof.

BACKGROUND ART

Calcium phosphates, such as hydroxyapatite, β-tricalcium phosphate (β-TCP), and octacalcium phosphate (OCP), are used as bone regeneration materials (e.g., PTL 1 to PTL 5). Moreover, PTL 5 proposes incorporating OCP into a porous body made of collagen so as to impart shape-retaining properties to the OCP. Furthermore, NPL 1 reports that a collagen porous body containing OCP has a more excellent bone-regeneration effect than OCP alone.

NPL 2 reports that local bone formation was significantly promoted by subcutaneous administration of parathyroid hormone (PTH). NPL 2 also reports that bone formation by β-TCP is limited, and that the bone-forming effect by PTH is inhibited by the combined use of PTH and β-TCP.

CITATION LIST

Patent Literature

PTL 1: JP2010-273847A
PTL 2: JP2003-260124A
PTL 3: JP2009-132601A
PTL 4: JP2005-279078A
PTL 5: JP2006-167445A
PTL 6: JP1993-070113A

Non-Patent Literature

NPL 1: Tissue ENGINEERING, Part A, 15, 1, 23-32-2009
NPL 2: J. Clin. Periodontol, 37: 419-426, 2010

SUMMARY OF INVENTION

Technical Problem

An object of the present invention is to provide a novel means effective for bone regeneration or bone augmentation.

Solution to Problem

It was confirmed that the combined use of a calcium phosphate-containing porous composite and PTH allowed more effective bone regeneration or bone augmentation. Based on this finding, inventions represented by the following items are provided.

A: Method of bone regeneration or augmentation A
A1. A method of bone regeneration or bone augmentation, comprising:
  implanting a porous composite at a site in need of the bone regeneration or bone augmentation, and
  administering parathyroid hormone (PTH) to a subject in need of the bone regeneration or bone augmentation,
  wherein the porous composite comprises calcium phosphate.
A2. The method of A1, wherein the porous composite is implanted, and then the PTH is administered.
A3. The method of A1 or A2, wherein the PTH is administered topically to the site in need of the bone regeneration or bone augmentation.
A4. The method of any one of A1 to A3, wherein the PTH is administered topically to the site where the porous composite has been implanted.
A5. The method of A1 or A2, wherein the PTH is administered subcutaneously.
A6. The method of any one of A1 and A3 to A5, wherein the PTH is administered to the subject, and then the porous composite is implanted.
A7. The method of A6, wherein the PTH is administered topically to the site in need of the bone regeneration or bone augmentation.
A8. The method of A6, wherein the PTH is administered subcutaneously.
A9. The method of any one of A1 to A8, wherein the site in need of the bone regeneration or bone augmentation is a site in need of the bone regeneration.
A10. The method of A9, wherein the site in need of the bone regeneration is a site of bone defect.
A11. The method of any one of A1 to A8, wherein the site in need of the bone regeneration or bone augmentation is a site in need of the bone augmentation.
A12. The method of A11, wherein the site in need of the bone augmentation is a site in need of at least one selected from the group consisting of sinus lift, bone graft, and ridge expansion.
A13. The method of any one of A1 to A12, wherein the porous composite further comprises collagen.
A14. The method of any one of A1 to A13, wherein the calcium phosphate is at least one selected from the group consisting of octacalcium phosphate (OCP), β-tricalcium phosphate (β-TCP), hydroxyapatite, and amorphous calcium phosphate.
A15. The method of any one of A1 to A14, wherein the PTH is teriparatide.

B: Method of bone regeneration or augmentation B
B1. A method of bone regeneration or bone augmentation, comprising:
  implanting a porous composite at a site in need of the bone regeneration or bone augmentation,
  wherein the porous composite comprises calcium phosphate and parathyroid hormone (PTH).
B2. The method of B1, wherein the site in need of the bone regeneration or bone augmentation is a site in need of the bone regeneration.
B3. The method of B2, wherein the site in need of the bone regeneration is a site of bone defect.
B4. The method of B1, wherein the site in need of the bone regeneration or bone augmentation is a site in need of the bone augmentation.
B5. The method of B4, wherein the site in need of bone augmentation is a site in need of at least one selected from the group consisting of sinus lift, bone graft, and ridge expansion.
B6. The method of any one of B1 to B5, wherein the porous composite further comprises collagen.
B7. The method of any one of B1 to B6, wherein the calcium phosphate is at least one selected from the group consisting of octacalcium phosphate (OCP), β-tricalcium phosphate (β-TCP), hydroxyapatite, and amorphous calcium phosphate.

B8. The method of any one of B1 to B7, wherein the PTH is teriparatide.

C: Composite with PTH

C1. A composite for bone regeneration or bone augmentation, comprising:
  calcium phosphate, and
  parathyroid hormone (PTH),
  wherein the composite is porous.

C2. The composite of C1, wherein the composite further comprises collagen.

C3. The composite of C1 or C2, wherein the calcium phosphate is at least one selected from the group consisting of octacalcium phosphate (OCP), β-tricalcium phosphate (β-TCP), hydroxyapatite, and amorphous calcium phosphate.

C4. The composite of any one of C1 to C3, wherein the PTH is teriparatide.

D: Method of producing a composite

D1. A method of producing a composite for bone regeneration or bone augmentation, comprising:
  adding parathyroid hormone (PTH) to a porous composite,
  wherein said porous composite comprises calcium phosphate.

D2. The method of D1, wherein the calcium phosphate is at least one selected from the group consisting of octacalcium phosphate (OCP), β-tricalcium phosphate (β-TCP), hydroxyapatite, and amorphous calcium phosphate.

D3. The method of D1 or D2, wherein the porous composite further comprises collagen.

D4. The method of any one of D1 to D3, wherein the PTH is teriparatide.

E: Kit

E1. A kit for bone regeneration or bone augmentation, comprising:
  (i) a porous composite comprising calcium phosphate, and
  (ii) parathyroid hormone (PTH).

E2. The kit of E1, wherein the calcium phosphate is at least one selected from the group consisting of octacalcium phosphate (OCP), β-tricalcium phosphate (β-TCP), hydroxyapatite, and amorphous calcium phosphate.

E3. The kit of E1 or E2, wherein the porous composite further comprises collagen.

E4. The kit of any one of E1 to E3, wherein the PTH is teriparatide.

Advantageous Effects of Invention

The present invention provides an effective means for bone regeneration and/or bone augmentation.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 3 shows low-magnification (×1.25) images.

FIG. 4 shows high-magnification (×20) images.

DESCRIPTION OF EMBODIMENTS

Figure 1:
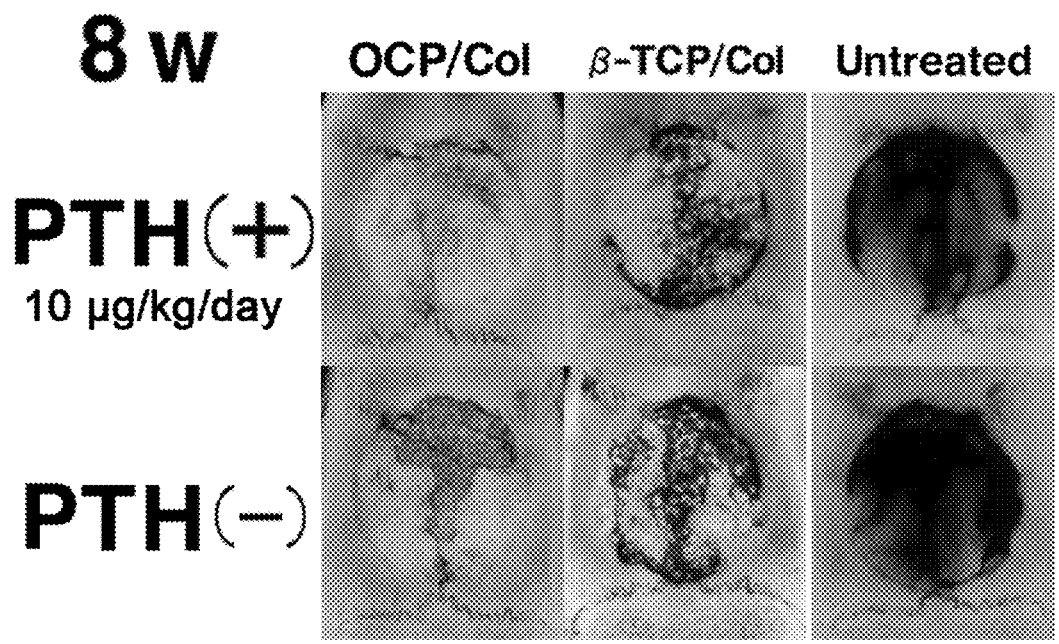
FIG. 1 shows X-ray photographs taken from above, showing the results of examining the influence of subcutaneously administered PTH on bone defect sites treated with an OCP-containing porous composite or a β-TCP-containing porous composite.

In one embodiment, the method of bone regeneration or bone augmentation preferably comprises:
  step (I) of implanting a porous composite containing calcium phosphate at a site in need of bone regeneration or bone augmentation; and
  step (II) of administering PTH to a subject in need of bone regeneration or bone augmentation.

Either step (I) or step (II) may be previously performed, or both steps may be performed at the same time. In the method of bone regeneration or bone augmentation according to one embodiment, step (II) is preferably performed after step (I). For example, PTH can be administered after the porous composite is implanted at a site in need of bone regeneration or bone augmentation. In the method of bone regeneration or bone augmentation according to another embodiment, step (I) is preferably performed after step (II). For example, PTH can be administered (e.g., by dropping) to a site in need of bone regeneration or bone augmentation, and then the porous composite can be implanted at the site.

PTH is generally called parathormone, parathyroid hormone, or parathyroid gland hormone, and is a human-derived polypeptide hormone comprising 84 amino acids secreted from the parathyroid (parathyroid gland). In this specification, the PTH includes not only wild-type PTH, but also derivatives having the same physiological function as wild-type PTH and pharmacologically acceptable salts thereof. Examples of such derivatives include teriparatide corresponding to a 34-amino-acid region of the N-terminal of wild-type PTH. Teriparatide is sold as a therapeutic agent for osteoporosis under the name of Forteo or Teribone, and has the amino acid sequence of SEQ ID NO: 1. In one embodiment, PTH is preferably teriparatide. The teriparatide mentioned herein also includes a pharmacologically acceptable salt thereof.

It is preferable that the porous composite contains calcium phosphate. Preferred calcium phosphate has a bone regeneration or bone augmentation effect. Examples of calcium phosphate include octacalcium phosphate (OCP), β-tricalcium phosphate (β-TCP), hydroxyapatite (HAP), amorphous calcium phosphate, dibasic calcium phosphate anhydrous (DCPA), dibasic calcium phosphate dihydrate (DCPD), and the like. In one embodiment, the calcium phosphate is preferably at least one member selected from the group consisting of OCP, β-TCP, and HAP, and more preferably OCP. These calcium phosphates can be prepared by any method, or commercial products can be purchased for use.

OCP can be prepared by various known methods. For example, OCP can be prepared by a drop method (LeGeros R Z, Calcif Tissue Int 37:194-197, 1985) or the method using a synthesizing apparatus (three-way pipe) disclosed in PTL 6. Alternatively, OCP can be prepared by a mixing method in which a sodium dihydrogen phosphate aqueous solution and a calcium acetate aqueous solution are mixed under appropriate conditions, and the produced precipitate is collected. The OCP obtained from the precipitate is preferably used after it is dried and ground with an electric mill, etc., into a granular powder. The particle size is preferably in the range of 10 to 1,000 μm, more preferably 100 to 500 μm, and even more preferably 300 to 500 μm. The particle size can be classified, for example, by sieving based on the opening size of the sieve.

β-TCP can be prepared by various known methods. For example, the following method can be used. First, a calcium hydroxide powder and a calcium hydrogen phosphate powder are mixed so that the molar ratio of calcium to phosphorus (Ca/P) is 1.45 to 1.72 to prepare a raw material powder. The obtained raw material powder is mixed and ground, and a calcium phosphate precursor is prepared by soft mechanochemical synthesis. The resulting precursor is heated at a temperature of 600° C. or more, thereby obtaining β-TCP. There is another method in which a mixed slurry containing calcium hydrogen phosphate and calcium carbonate is ground and reacted in a pot mill for 24 hours, and the slurry is dried, followed by firing at 750° C. for 1 hour, thereby obtaining a β-TCP powder.

HAP can be prepared by various known methods. For example, a hydrothermal synthesis method, a dry synthesis method, or a wet synthesis method can be used. The hydrothermal synthesis method is as follows. The pH of an aqueous suspension of dibasic calcium phosphate anhydrous ($CaHPO_4$) is adjusted to 4 using phosphoric acid ($H_3PO_4$). Then, the suspension is reacted in a hydrothermal synthesis apparatus at 350° C. at 8,800 lb/in$^2$ for 48 hours, thereby obtaining HAP. The dry synthesis method is as follows. HAP can be obtained by reacting calcium pyrophosphate ($Ca_2P_2O_7$) or tricalcium phosphate ($Ca_3(PO_4)_2$), which are poorly-soluble calcium phosphates, with calcium carbonate ($CaCO_3$) in a steam atmosphere at 900 to 1,300° C. for 1 to 24 hours. The wet synthesis method is as follows. HAP can be obtained by reacting an aqueous solution of soluble phosphate or phosphoric acid, and an aqueous solution of soluble calcium salt at 70 to 100° C. for 24 to 48 hours while maintaining alkalinity. In another wet synthesis method, HAP can be obtained by suspending a water-insoluble calcium phosphate salt in water, adding water-insoluble calcium carbonate ($CaCO_3$) to the suspension, and reacting the suspension by overheating while stirring. In still another wet synthesis method, HAP can be obtained by mixing a calcium carbonate powder and a powder of calcium hydrogen phosphate or a dihydrate thereof so that the atomic ratio of calcium atoms to phosphoric acid is within the range of 1.5 to 1.67, and grinding and mixing the mixture using a wet grinding mill.

The material of the porous composite is any material and is not particularly limited, as long as it is suitable for bone regeneration or bone augmentation. For example, the porous composite may be calcium phosphate formed in a porous state. In one embodiment, when the porous composite is formed of calcium phosphate, the calcium phosphate is preferably β-TCP or HAP. In one embodiment, the porous composite is preferably formed of collagen and calcium phosphate.

The source, properties, etc., of the collagen constituting the porous composite are not particularly limited, as long as it is suitable as a material for bone regeneration or bone augmentation, and any collagen can be used. In one embodiment, the collagen is preferably enzyme-soluble collagen obtained by solubilizing collagen with protease (e.g., pepsin or pronase) to remove telopeptide. Such collagen is less allergenic. Moreover, the collagen is preferably fibrous collagen, i.e., type-I, type-II, type-III, or type-IV collagen. In one embodiment, the collagen is preferably type-I collagen, which is contained in a large amount in the living body, or a mixture of type-I collagen and type-III collagen. Examples of the raw material of the collagen include skin, bone, or tendon of pigs or cows, scales of fish, and the like. Collagen is an organism-derived component, and is thus highly safe. Commercially available collagen can also be used.

When the porous composite is formed of collagen, the proportion of calcium phosphate and collagen can be suitably adjusted in consideration of the desired shape-retaining properties, operability, biocompatibility, etc. For example, the mixing ratio of calcium phosphate to 1 part by weight of collagen is 0.5 to 35 parts by weight, preferably 1 to 20 parts by weight, and more preferably 2 to 10 parts by weight. If the amount of calcium phosphate is less than 0.5 parts by weight based on 1 part by weight of collagen, the obtained composite may have an inferior bone regeneration function. If the amount of calcium phosphate is more than 35 parts by weight, shape-retaining properties may be reduced. The calcium phosphate used herein is preferably OCP.

In one embodiment, the porous composite preferably has a pore size of 3 to 90 μm. If the pore size exceeds 90 μm, the strength of the porous composite tends to decrease. On the other hand, if the pore size is less than 3 μm, bone metabolism cells, such as osteoblastic cells, are less likely to enter, and the effect of promoting bone regeneration may be reduced. The pore size of the porous composite is more preferably 5 to 40 μm, and even more preferably 7 to 36 μm.

The pore size of the porous composite is measured by pore distribution measurement using a mercury porosimeter. The specific measurement method is as follows.

Measurement of Pore Size

As a pretreatment, samples (porous composites) are dried at a constant temperature of 120° C. for 4 hours. Each of the pretreated samples is measured for the distribution of the pore size (0.0018 to 200 μm) by a mercury penetration method using the following measuring apparatus under the following conditions:

Measuring apparatus: AutoPore IV9520 (produced by Micromeritics)

Measurement condition: contact angle between mercury and sample: 140 deg

Surface tension of mercury: 0.48 N/m (in terms of 1 dyne=10-5N)

In the pore distribution curve obtained by the mercury penetration method mentioned above, the value of the pore size (diameter) showing the maximum peak having the largest area is the value of the pore size in this specification.

In one embodiment, the porous composite satisfies the condition that, in the pore distribution measured by the mercury penetration method, the proportion of pores of a size of 71 to 200 μm in all of the pores of a size of 200 μm or less is preferably 8% or less, and more preferably 3 to 8%. The pore ratio is represented by the following formula using the cumulative pore volume and entire pore volume measured by the mercury porosimeter:

Pore ratio (%)=cumulative pore volume/entire pore volume×100

The porosity (void ratio) of the porous composite is preferably 80 to 98%, more preferably 85 to 95%, and still more preferably 85 to 90%. The porosity is determined by the following formula using the entire pore volume and apparent density measured by the mercury penetration method:

Porosity (%)=entire pore volume/{(1/apparent density)+entire pore volume}×100

The shape of the porous composite can be freely determined in consideration of the shape, size, etc., of the affected part in which the porous composite is placed. For example, the porous composite is preferably in the form of a rectangular parallelepiped (block), a cube, a cylinder, tablets, or granules. In one embodiment, the size of the porous composite having a rectangular parallelepiped shape is preferably 5 mm×5 mm×5 mm or more. In general, the upper limit is preferably 100 mm×100 mm×100 mm. When the porous composite has a cylindrical shape, the size thereof is preferably such that the diameter is 5 to 50 mm, and the height is in the range of 1 to 50 mm. When the porous composite has a granular shape, the shape is not limited to spherical, and may be amorphous; however, the diameter is preferably 0.1 to 10 mm. The diameter of the granular porous composite is determined by a sieve analysis method.

The manner of implanting the porous composite is any manner, and is not particularly limited. For example, the porous composite is implanted by filling a site in need of bone regeneration or bone augmentation with the porous composite of a suitable size. When sufficient blood or body fluid is present in the site in need of bone regeneration or bone augmentation (e.g., bone defect site), the porous composite can be filled therein as it is or after being cut into a suitable shape. When sufficient blood, etc., is not observed in the site, or when the porous composite in the original shape cannot be filled in the site, the porous composite can be filled in the bone defect site after the porous composite is immersed in blood or physiological saline, and confirmed to have sponge-like elasticity.

The manner of administering PTH is any manner, and is not particularly limited. For example, PTH is administered topically or systemically by any method. In one embodiment, PTH is preferably administered topically to a site in need of bone regeneration or bone augmentation (e.g., bone defect site). Topical administration can be performed, for example, by dropping a solution containing PTH on the site. When PTH is topically administered after the porous composite is implanted, for example, the PTH can be administered on the porous composite implanted in a site in need of bone regeneration or bone augmentation. PTH can be topically administered to the site, for example, by surgically exposing the site during bone regeneration or bone augmentation surgery, and dropping a solution containing PTH thereon. Alternatively, PTH can be topically administered to the site by inserting an injection needle into the site, and injecting a solution containing PTH. In one embodiment, PTH is administered systemically by injection. For example, PTH is administered by subcutaneous injection, intramuscular injection, or intravenous injection. In one embodiment, PTH is preferably administered systemically by subcutaneous injection.

The amount of PTH administered is freely determined and is not particularly limited. For example, the amount of PTH can be suitably determined depending on the degree of bone defect, the body weight and age of the subject, etc. When a liquid containing PTH is dropped on a site in need of bone regeneration or bone augmentation, the concentration of PTH in the liquid is 0.01 μg/mL to 500 μg/mL, for example. Moreover, the amount of the PTH-containing solution dropped on the site is 0.01 mL to 500 mL, for example. The PTH-containing solution can be prepared, for example, by adding a commercially available PTH (e.g., teriparatide) to physiological saline. When PTH is administered systemically by injection, its dosage can be set as 0.01 μg/kg/day to 50 μg/kg/day, for example. The PTH administration may be performed once or multiple times. In one embodiment, when PTH is systemically administered, the PTA is preferably administered multiple times for a certain period of time. For example, the administration frequency is once a day, once a week, 2 times to 6 times a week, or 1 time to 3 times a month. The dosing period is, for example, one week, one month, two to eleven months, one year, one year and a half, or two to five years.

The site in need of bone regeneration includes a bone defect site, for example. Bone defects can be caused by various factors. Examples of factors of bone defects include bone fracture, post-traumatic bone loss, bone surgery, congenital bone loss, and post-infectious bone loss; bone deficit conditions associated with bone chemotherapy treatment, allograft incorporation, and bone radiotherapy treatment; periodontal disease; and the like. Examples of bone surgery include spinal fusion surgery, arthrodesis including extremity arthrodesis, etc., post-traumatic bone surgery, post-prosthetic joint surgery, post-plastic bone surgery, dental surgery, and the like. In one embodiment, examples of bone defect sites include a cystic cavity, an atrophic alveolar ridge, a cleft jaw, a tooth-extraction cavity, and the like.

The site in need of bone augmentation is not particularly limited. Examples thereof include sites in need of at least one treatment selected from the group consisting of sinus lift, bone graft, and ridge expansion. In one embodiment, the site in need of bone augmentation can be a site that shows pathological conditions of reduction in bone mineral content associated with osteoporosis, spondylosis deformans, rheumatoid arthritis, malignancy, trauma, etc. In another embodiment, examples of the site in need of bone augmentation include oral surgery pathological conditions associated with dysphemia, dysmasesis, and/or aesthetic defects.

Examples of the subject include, but are not particularly limited to, humans, dogs, cats, monkeys, rats, and like animals. In one embodiment, the subject is preferably a human.

In one embodiment, the above porous composite preferably contains calcium phosphate and PTH. In other words, in one embodiment, PTH is preferably administered in a state of being incorporated into the porous composite. The porous composite containing PTH can be produced by any method. For example, a PTH-containing porous composite can be obtained by preparing a porous composite that does not contain PTH, and dropping a PTH-containing solution thereon, or by immersing a porous composite that does not contain PTH in a PTH-containing solution. Such a PTH-containing porous composite may be prepared immediately before the implantation of the porous composite, or may be previously prepared and stored until use.

The amount of PTH contained in the porous composite is any amount, and is not particularly limited. For example, the porous composite can contain 40 μg/g to 25 mg/g of PTH.

In one embodiment, a kit for bone regeneration or bone augmentation comprising the above porous composite and PTH is provided. The kit may comprise any of the above-described porous composites. In addition to the porous composite and PTH, the kit may further comprise any components, reagents, instructions, etc.

The porous composite can be produced by any method. For example, the porous composite can be produced by the following methods (a) to (c). The following methods are described using OCP as the calcium phosphate; however, when other calcium phosphate is used, a porous composite can also be obtained in the same manner. When β-TCP is used as the calcium phosphate, method (a) or (b) is preferred.

(a) Method for Forming a Composite by Mixing OCP and Collagen

OCP is added to a collagen solution whose concentration, pH, etc., are adjusted to a range in which gelation can occur, and they are sufficiently kneaded to prepare a mixture of OCP and collagen. Then, the mixture is molded in a suitable mold, frozen, and freeze-dried to obtain a composite. The obtained composite is preferably subjected to heat dehydration crosslinking treatment, and sterilized by a conventional sterilization method (e.g., γ-ray irradiation, electron beam irradiation, or ethylene oxide gas).

(b) Method for Forming a Composite by Mixing an OCP Suspension

The pH of a collagen acidic solution with a suitable concentration is aseptically adjusted to 5.5 to 7.5 using a suitable buffer (e.g., phosphate buffer, tris buffer, or sodium acetate buffer). OCP is added thereto before the collagen is gelled, thereby preparing a suspension of collagen and OCP. Thereafter, the suspension is poured into a mold while maintaining a neutral to weakly alkaline pH. After molding, the suspension is gelled at a suitable temperature (e.g., 37° C.), and water washing is repeated to remove salts, such as buffers. A composite can be thus obtained. Thereafter, the composite is preferably subjected to freeze drying and sterilization, as in method (a) mentioned above.

(c) Method for Forming a Composite by Depositing OCP on Collagen

The pH of a collagen acidic solution with a suitable concentration is aseptically adjusted to 5.5 to 7.5 using a suitable buffer (e.g., phosphate buffer, tris buffer, or sodium acetate buffer). A calcium solution and a phosphoric acid solution are added thereto before the collagen is gelled, thereby depositing the OCP on the collagen. Subsequently, while maintaining a neutral to slightly alkaline pH, the deposited OCP is poured into a mold, and molded. Gelation is performed at a suitable temperature (e.g., 37° C.), and water washing is repeated to remove salts, such as buffers. A composite can be thus obtained. Thereafter, the composite is preferably subjected to freeze drying and sterilization, as in method (a) mentioned above.

The deposition of OCP is based on the concentrations of $Ca^{2+}$ and $PO_4^{3-}$, and the degree of supersaturation (ionic product/solubility product) determined by pH, etc. Therefore, the OCP can be deposited by pouring a $Ca^{2+}$ solution and a $PO_4^{3-}$ solution into a collagen solution whose pH is adjusted, under conditions in which OCP is oversaturated. The OCP is spontaneously deposited in the collagen gap, or deposited using the surface of the collagen fiber as the core.

In one embodiment, the method of producing the porous composite preferably comprises a step of freeze-drying after a gel, sol, or liquid containing OCP and collagen is frozen by immersion in a liquid refrigerant. The phrase "a gel, sol, or liquid containing OCP and collagen is frozen by immersion in a liquid refrigerant" includes, for example, an embodiment in which a container containing the gel, sol, or liquid is sealed, and then immersed in a liquid refrigerant to freeze the gel, sol, or liquid.

The liquid refrigerant is a liquid having a temperature lower than the freezing point of the gel, sol, or liquid containing OCP and collagen. Examples include methanol, ethanol, acetone, acetonitrile, liquid nitrogen, and the like. The temperature of the liquid refrigerant is preferably −20° C. or less, more preferably −40° C. or less, and even more preferably −80° C. or less. It is considered that the pore size of the porous composite to be obtained can be reduced by rapidly freezing the gel, sol, or liquid containing OCP and collagen by immersion in the liquid refrigerant.

In one embodiment, the porous composite is preferably subjected to heat treatment. Due to the heat treatment, part of the OCP molecular structure is broken, and bone-forming cells are more likely to enter. Thus, bone regeneration is promoted, and the collagen is crosslinked to improve shape-retaining properties.

The temperature of heat treatment is preferably 50 to 200° C., and more preferably 60 to 180° C. Moreover, the heat treatment is preferably performed at reduced pressure. The pressure is preferably 0 to 3,000 Pa, and more preferably 0 to 300 Pa. The time of heat treatment is preferably 0.1 to 10 days, and more preferably 0.5 to 5 days.

The porous composite using HAP can be obtained, for example, by the following method. First, a phosphoric acid (salt) aqueous solution and a calcium salt aqueous solution or suspension are prepared. A collagen/phosphate aqueous solution is prepared using collagen, and phosphoric acid or phosphate, such as disodium hydrogen phosphate, sodium dihydrogen phosphate, dipotassium hydrogen phosphate, or potassium dihydrogen phosphate. A calcium salt aqueous solution or suspension is prepared using calcium carbonate, calcium acetate, calcium hydroxide, or the like. Water in an amount almost the same as the amount of the calcium salt aqueous solution or suspension to be added is previously placed in a reaction vessel, and heated to about 40° C. The collagen/phosphate aqueous solution and the calcium salt aqueous solution or suspension are simultaneously dropped thereon at room temperature, thereby forming a fibrous HAP/collagen composite. After the completion of dropping, the mixture of water and the HAP/collagen composite in the form of slurry is freeze-dried. Freeze drying is carried out by performing vacuum suction in a frozen state at −10° C. or lower, and performing rapid drying. Thereafter, a crosslinking treatment is performed to thereby obtain a porous composite containing HAP and collagen.

In one embodiment, the porous composite may contain any components other than the above-mentioned components. Examples of such components include bioabsorbable polymers (polyglycolic acid, polylactic acid, polylactic acid-polyethylene glycol copolymer, etc.).

The above-mentioned porous composites can be used as bone regeneration material. Such bone regeneration materials are useful for bone defect recovery in the dental oral surgery field and orthopedic surgery field, and for bone defect recovery after craniotomy or thoracotomy. For example, in the dental oral surgery field, when a bone defect caused by periodontal disease, a cystic cavity, an atrophic alveolar ridge, a cleft jaw, a tooth-extraction cavity, or the like is filled with a bone regeneration material comprising the porous composite, an excellent bone regeneration effect can be confirmed after several weeks to several months. In the orthopedic surgery field, for example, in the case of a bone defect after resection of a bone tumor or a bone defect caused by trauma, such as a bone fracture, the bone defect site can be filled with the bone regeneration material to thereby promote bone regeneration.

EXAMPLES

The present invention is described in more detail below with reference to Examples; however, the present invention is not limited thereto.

Production Example 1: Preparation of OCP

Liquid 1 and liquid 2 for preparation of OCP were prepared in the following manner. Sodium dihydrogen phosphate dihydrate (31.2 g) was dissolved in 2,500 g of distilled water to prepare liquid 1. Calcium acetate monohydrate (35.2 g) was dissolved in 2,500 g of distilled water to prepare liquid 2. Liquid 1 was placed in a separable flask, and heated to 70° C. using a mantle heater. While stirring liquid 1 at a rate of 250 rpm using a stirrer (MAZELA Z, produced by Tokyo Rikakikai Co., Ltd.) to which a stirring blade (blade diameter: 12 cm) was attached, liquid 2 was dropped at a rate of about 28 mL/min. After the completion of dropping, the mixture of liquid 1 and liquid 2 was further stirred at 70° C. at 250 rpm for 2 hours.

The precipitate produced in the above mixture was filtered through a membrane filter (pore size: 3 μm; A300A293C, produced by Advantec Toyo Kaisha, Ltd.), and collected. The collected precipitate was dispersed in 1,500 mL of distilled water, and washed by stirring for 15 minutes. The process of filtering and washing was further repeated 3 times. The washed precipitate was dried in a constant temperature dryer at 30° C. for 24 hours. After the dried precipitate was ground with an electric mill, the ground product was classified using a sieve to a particle size of 300 to 500 μm. Thus, a powder was obtained. Finally, the obtained powder was subjected to dry sterilization at 120° C. for 2 hours, thereby obtaining OCP.

Production Example 2: Preparation of OCP/Collagen Complex

Pig dermis-derived collagen containing type-I collagen and type-III collagen (NMP Collagen PS, produced by NH Foods Ltd.; 1 part by weight) was dissolved in 200 parts by weight of distilled water that was cooled to 4° C., thereby obtaining about 0.5 wt. % of a collagen solution. While maintaining the solution temperature at 4° C., a sodium hydroxide aqueous solution was added to the collagen aqueous solution, and the pH was adjusted to about 7.4 to obtain a collagen suspension. The ionic strength of the collagen suspension at this time was about 0.01. The OCP (particle size: 300 to 500 μm) obtained in Production Example 1 was added to the collagen suspension so that the weight ratio of OCP to collagen was 77:23. The mixture was stirred at room temperature, thereby obtaining an OCP/collagen suspension.

The OCP/collagen suspension was placed in a centrifuge bottle, and centrifuged by a centrifugal separator (GRX-250, produced by Tomy Seiko Co., Ltd.) at a centrifugal force of 7,000×g for 20 minutes. After the supernatant was discarded so that the amount of collagen in the OCP/collagen suspension was 3 wt. %, the content was mixed with a drug spoon for about 2 minutes to obtain an OCP/collagen complex gel. The gel was placed in a plastic container (inner diameter: 9.0 mm, volume: about 3.0 cm$^3$) having a cylindrical inner space, and centrifuged at a centrifugal force of 230×g for 1 minute, followed by defoaming.

The sealed plastic container was immersed in methanol cooled to −80° C. in a large excess amount relative to the volume of the container for rapid freezing. After the container was opened, the frozen product was dried by a freeze dryer (−10° C., 48 hours) and molded. Subsequently, the molded product was heated at 150° C. for 24 hours at reduced pressure to perform thermal dehydration crosslinking. The resulting product was cut with a scalpel to a thickness of 1.0 mm (used in Test Example 1) or 1.5 mm (used in Test Example 2). The cut pieces were sterilized by electron beam irradiation to obtain OCP/collagen complexes.

Production Example 3: Preparation of β-TCP/Collagen Complex

A β-TCP/collagen complex was obtained in the same manner as in Production Example 2, except that β-TCP (OSferion, produced by Olympus Terumo Biomaterials Corp.) granulated to a diameter of 300 to 500 μm was used in place of the OCP.

Production Example 4: Preparation of Teriparatide for Dropping

Physiological saline (1.13 mL) was added to 56.5 μg of a subcutaneous injection formulation of Teribone (produced by Asahi Kasei Pharma Corporation) to obtain a 50 μg/mL teriparatide (PTH) solution. The teriparatide solution (20 μL) was taken in a PCR tube (0.5 mL), and 80 μL of physiological saline was added thereto to obtain 1.0 μg/0.1 mL (10 μg/mL) teriparatide solution. This solution was further diluted 10 times with physiological saline to obtain 0.1 μg/0.1 mL (1.0 μg/mL) teriparatide solution. These were stored in a freezer at −20° C. until use.

Production Example 5: Preparation of Teriparatide for Subcutaneous Injection

Physiological saline (1.13 mL) was added to 56.5 μg of a subcutaneous injection formulation of Teribone (produced by Asahi Kasei Pharma Corporation) to obtain a 50 μg/mL teriparatide solution. The teriparatide solution (70 μL) was taken in a PCR tube (0.5 mL), and 280 μL of physiological saline was added thereto to obtain a 3.5 μg/0.35 mL (10 μg/mL) teriparatide solution. These were stored in a freezer at −20° C. until use.

Production Example 6: Production of OCP/FGF-2 Composite (OCP/FGF-2)

Freeze-dried recombinant human Fibroblast growth factor-2 (FGF-2, produced by R & D Systems) was dissolved in a 0.01 M phosphate buffer (containing 0.1% or more bovine serum albumin and 1 mM DTT (dithiothreitol)). FGF-2 was added to 15 mg of dry-sterilized OCP granules (diameter: 300 to 500 μm) at three different concentrations (10 ng, 100 ng, and 1 μg). After immersion at −20° C. for 20 minutes, the resultant was freeze-dried to prepare OCP/FGF-2. As a control sample, OCP granules to which FGF-2 was not added were used.

Test Example 1: OCP or β-TCP+Teriparatide (Subcutaneous Injection)

Male Wistar rats (12 weeks old) were each intraperitoneally anesthetized, and a skin incision and a periosteal incision were made in the calvarium part to expose the calvarium. A standardized full-thickness bone defect (diameter: about 9 mm), for which spontaneous recovery could not be expected, was created. Then, one OCP/collagen composite disc produced in Production Example 2 or one β-TCP/collagen composite disc produced in Production Example 3 was implanted therein. As the control, rats in which only a bone defect was created, and no sample was implanted (untreated group) were prepared. After the sample was implanted, the periosteum and skin were sutured, and the surgery was completed. The OCP/collagen group, the β-TCP/collagen group, and the untreated group were each divided into a teriparatide subcutaneous injection group (subcutaneous injection group) and a group that did not undergo teriparatide subcutaneous injection (non-injection group); they were divided into 6 groups in total. In the rats of the teriparatide subcutaneous injection group, 10 μg/kg of the teriparatide prepared in Production Example 5 was subcutaneously injected immediately after surgery and every day thereafter. Subcutaneous injection was performed in such a manner that the thawed teriparatide solution was sucked by a 1-mL syringe (27 G injection needle), the back skin was sterilized with a dilute Hibitane solution, and then a considerable amount of teriparatide solution was injected subcutaneously in the back. The observation period after surgery was 8 weeks for each group, and 5 rats were used in each period.

Four weeks and eight weeks after surgery, tomography was carried out on the rats in the living state using an X-ray CT scanner for experimental animals (Latheta LCT-200, produced by Hitachi Aloka Medical, Ltd.) at a low X-ray tube voltage, and the state of new bone formation in the bone defect site was carefully examined. Similarly, after CT photography 8 weeks after surgery, the rats were euthanized under anesthesia with an excess amount of pentobarbital. The calvarium and surrounding tissue were taken, and immersed and fixed in 0.1 M phosphate-buffered 4% paraformaldehyde (pH 7.4). The extracted samples were photographed (20 kV, 5 mA) by a soft X-ray camera (CMBW-2, produced by Softex Co., Ltd.), and then decalcified with 10% EDTA to prepare paraffin samples. Then, tissue sections (thickness: 6 μM) cut in the frontal plane were prepared, and a histological search was performed by hematoxylin-eosin staining. Further, using the plural tissue sections corresponding to the center of the defect of each sample, the ratio of new bone (n-Bone %) in the created defect was examined by histological quantification. Variance analysis, etc., were conducted using the average value and standard deviation of n-Bone % in each group, and a significance test was conducted. The significance level was set at 5%.

FIGS. 1 to 5 show the results. In each of FIGS. 1 to 4, PTH (+) represents a group to which teriparatide was subcutaneously administered, and PTH (−) represents a group to which teriparatide was not administered. FIG. 1 shows X-ray photographs of the bone defect sites of the rats photographed in the living state. In the OCP/Col/PTH subcutaneous injection group, a massive radiopaque image was observed in the entire defect, and the radiopaque image covered a wider range of the defect than the OCP/Col group. As is similar in the β-TCP/Col/PTH subcutaneous injection group, an opaque image covered a wider range of the defect than the β-TCP/Col group. In contrast, in the untreated/PTH subcutaneous injection group and the untreated group, radiopaque images in the defects were equally scarce.

Figure 2:
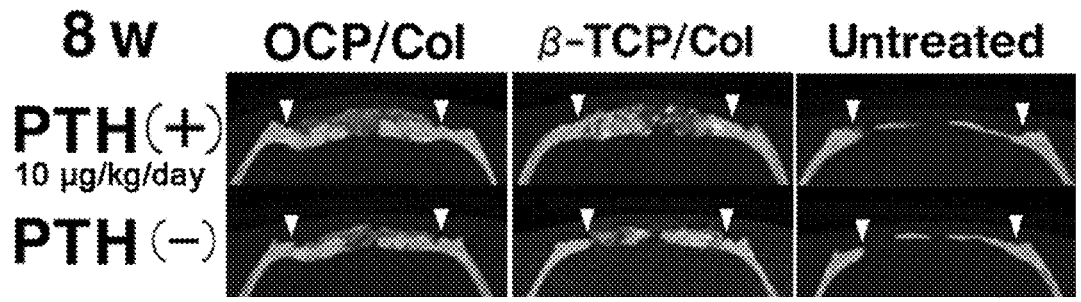
FIG. 2 shows X-ray photographs showing the results (cross sections) of examining the influence of subcutaneously administered PTH on bone defect sites treated with an OCP-containing porous composite or a β-TCP-containing porous composite.

FIG. 2 shows X-ray photographs of the calvarium and the surrounding tissue. In the OCP/Col/PTH subcutaneous injection group, a wider range of the defect was covered with an radiopaque image similar to that of the existing bone, compared with the OCP/Col group. In the β-TCP/Col/PTH subcutaneous injection group, a wider range of the defect was also covered with an radiopaque image similar to that of the existing bone, compared with the β-TCP/Col group. β-TCP, which was more radiopaque than that of the existing bone, was scattered in the defect; some were surrounded by the radiopaque image, and others were isolated. In the untreated/PTH subcutaneous injection group and the untreated group, radiopaque images extending from the defect margins (∇) were observed; however, their thickness was thinner than that of the existing bone.

Figure 3:
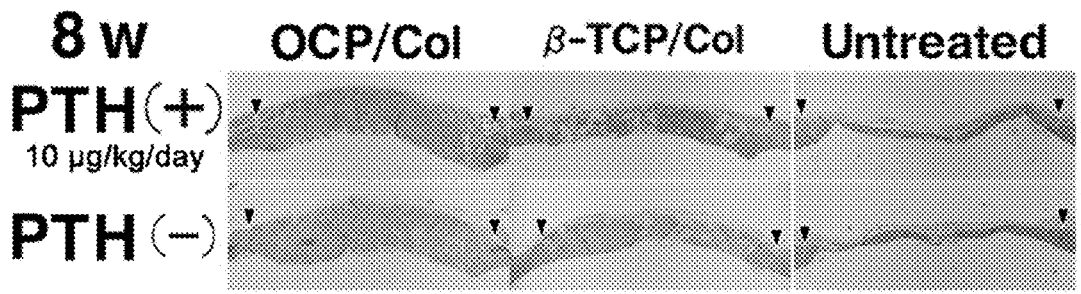
FIG. 3 shows the results of examining the influence of subcutaneously administered PTH on bone defect sites treated with an OCP-containing porous composite or a β-TCP-containing porous composite, using stained pathological specimens. The upper side is the skin side, and the lower side is the endocranial side. Black triangles (▼) indicate defect margins.
Figure 4:
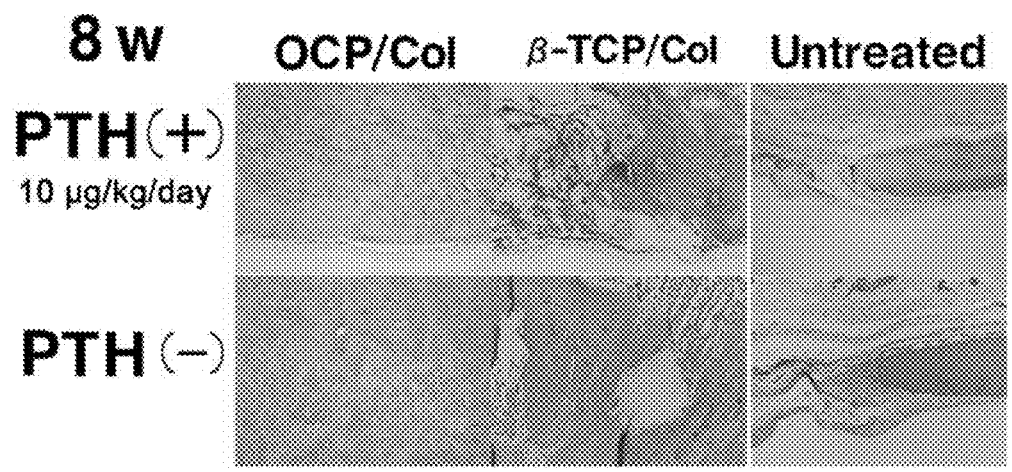
FIG. 4 shows the results of examining the influence of subcutaneously administered PTH on bone defect sites treated with an OCP-containing porous composite or a β-TCP-containing porous composite, using stained pathological specimens. The upper side is the skin side, and the lower side is the endocranial side. Black triangles (▼) indicate defect margins.

FIGS. 3 and 4 show stained pathological specimens. The upper side of each pathological specimen is the skin side, and the lower side is the endocranial side. In FIG. 3, which shows low-magnification (×1.25) images, a large part of the inside of the defect of the OCP/Col/PTH subcutaneous injection group was filled with red-stained new bone, and the thickness was maintained. In the OCP/Col group, the β-TCP/Col/PTH subcutaneous injection group, and the β-TCP/Col group, new bone and the implant were both present in the inside of the defects. In the untreated/PTH subcutaneous injection group and the untreated group, the inside of the defects was made of thin bone tissue extending from the defect margins (▼) and connective tissue surrounding the bone tissue. In FIG. 4, which shows high-magnification (×10) images, in the OCP/Col/PTH subcutaneous injection group and the OCP/Col group, the new bone integrated with the implanted OCP/Col had a mosaic form. Positive bone modification was suggested, and blood vessel invasion into the new bone was also observed. Moreover, the implanted OCP granules were smaller. In the β-TCP/Col/PTH subcutaneous injection group and the β-TCP/Col group, new bone surrounded the β-TCP granules, and part of the granules was contained in the new bone. However, the size of the remaining β-TCP granules appeared to be larger than that of the OCP granules. In the untreated/PTH subcutaneous injection group and the untreated group, thin new bone extended from the defect margins.

Figure 5:
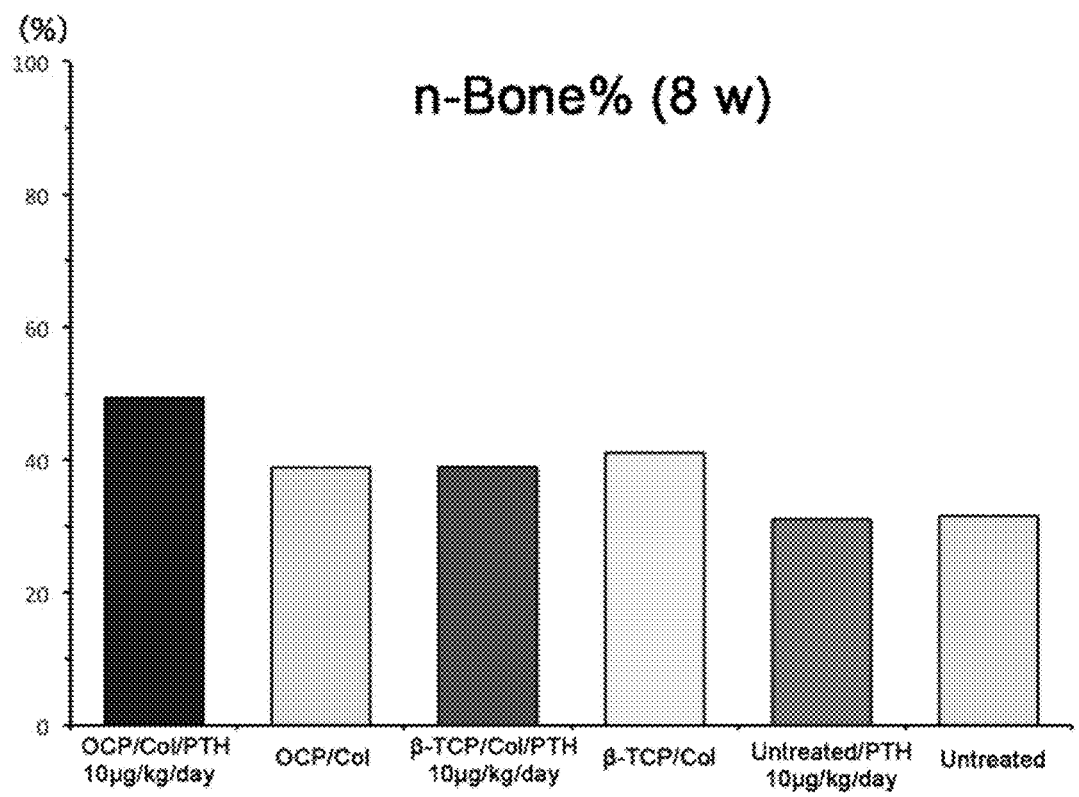
FIG. 5 shows the results of examining the influence of subcutaneously administered PTH on bone defect sites treated with an OCP-containing porous composite or a β-TCP-containing porous composite, based on the ratio of new bone (n-Bone %).

Using the plural tissue sections corresponding to the center of the defect of each sample, the ratio of new bone (n-Bone %) in the defect was examined by histological quantification (FIG. 5). The results were as follows: OCP/Col/PTH subcutaneous injection group: 49.3±8.4, OCP/Col group: 38.8±14.7, β-TCP/Col/PTH subcutaneous injection group: 39.0±17.6, β-TCP/Col group: 41.0±11.9, untreated/PTH subcutaneous injection group: 31.1±10.2, and untreated group: 31.6±11.9. Thus, the OCP/Col/PTH subcutaneous injection group showed a higher value than that of the OCP/Col group. In contrast, the β-TCP/Col/PTH subcutaneous injection group and the untreated/PTH subcutaneous injection group each showed a new bone ratio similar to those of the β-TCP/Col group and the untreated group, respectively.

As described above, the results of FIGS. 1 to 5 confirmed that although new bone formation was not observed when teriparatide was used alone, new bone formation was significantly promoted by the combined use of teriparatide with OCP or β-TCP, as compared with when OCP or β-TCP was used alone.

Test Example 2: OCP or β-TCP+Teriparatide (Dropping)

Male Wistar rats (12 weeks old) were each intraperitoneally anesthetized, and a skin incision and a periosteal incision were made in the calvarium part to expose the calvarium. A standardized full-thickness bone defect (diameter: about 9 mm), for which spontaneous recovery could not be expected, was created. Then, one OCP/collagen composite disc produced in Production Example 2 or one β-TCP/collagen composite disc produced in Production Example 3 was implanted therein. In this case, the teriparatide solution (1.0 μg/0.1 mL or 0.1 μg/0.1 mL) prepared in Production Example 4 was dropped on the OCP/collagen composite disc, and the same teriparatide solution (1.0 μg/mL) was dropped on the β-TCP/collagen composite disc. As the control, a group in which the teriparatide solution was not dropped on the OCP/collagen composite disc or β-TCP/collagen composite disc was prepared. After the sample was implanted, the periosteum and skin were sutured, and the surgery was completed. The observation period after surgery was 12 weeks for each group, and 6 rats were used in each period. The same analysis as in Test Example 1 was conducted 4 weeks and 12 weeks after surgery.

Figure 6:
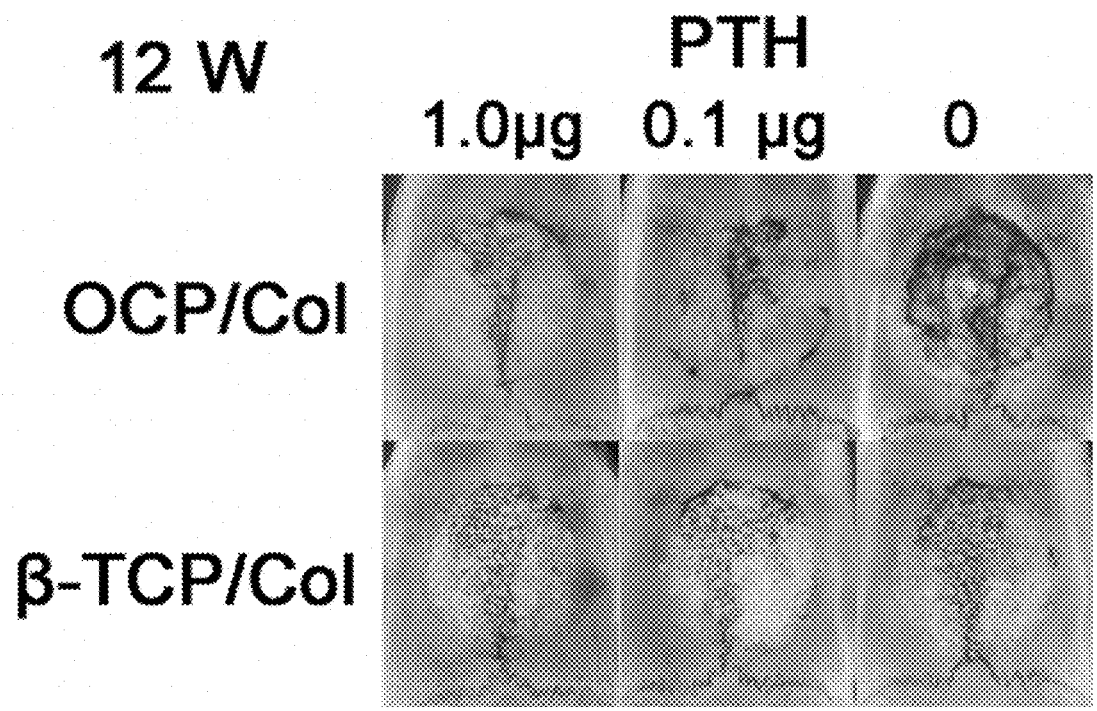
FIG. 6 shows X-ray photographs taken from above, showing the results of examining the influence of PTH dropped on bone defect sites treated with an OCP-containing porous composite or a β-TCP-containing porous composite.

FIGS. 6 to 9 show the results. FIG. 6 shows X-ray photographs of the bone defect sites of the rats photographed by the excised specimen. In the OCP/Col/PTH 1.0 μg/0.1 mL dropping group and the OCP/Col/PTH 0.1 μg/0.1 mL dropping group, the entire defect was covered with a plate-like radiopaque image. In the OCP/Col group, a large part of the defects was covered with a massive radiopaque image, and transmission images were partially present. These results confirmed that new bone formation by OCP was significantly promoted by dropping PTH. In the β-TCP/Col/PTH 1.0/0.1 mL dropping group and the β-TCP/Col/PTH 0.1 μg/0.1 mL dropping group, it was also confirmed that the entire defect was covered with a plate-like radiopaque image.

Figure 7:
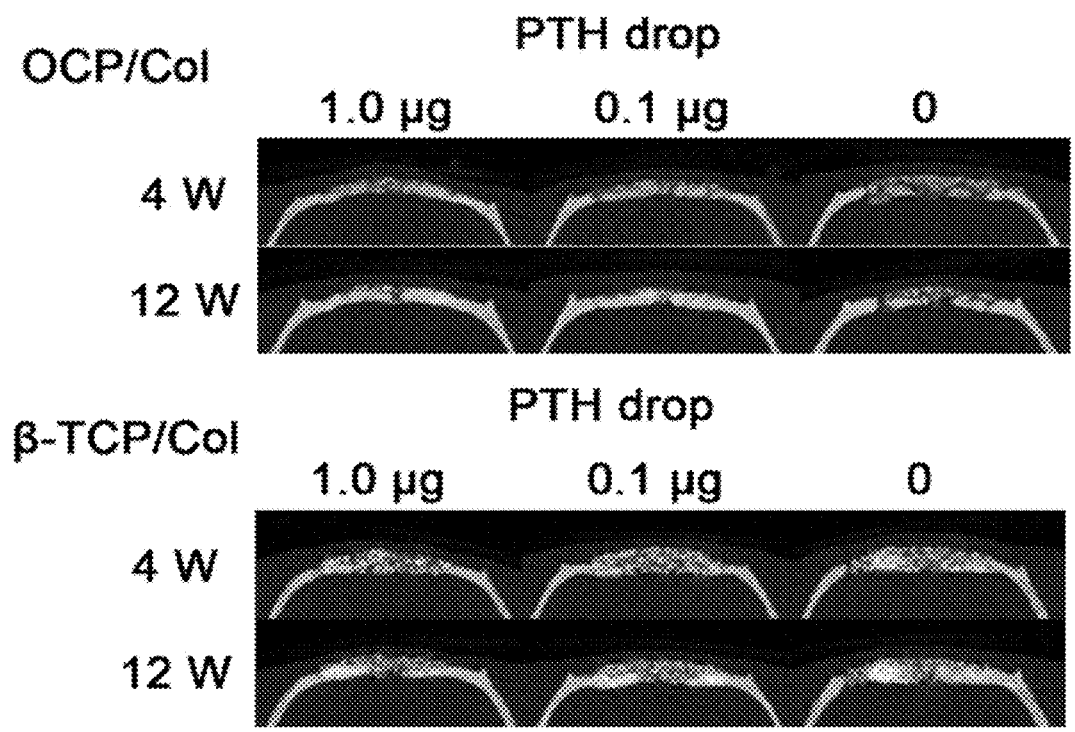
FIG. 7 shows X-ray photographs showing the results (cross sections) of examining the influence of PTH dropped on bone defect sites treated with an OCP-containing porous composite or a β-TCP-containing porous composite.

FIG. 7 shows X-ray photographs of the calvarium and the surrounding tissue in the living state. The upper photographs show the results of the OCP/Col/PTH 1.0 μg/0.1 mL dropping group, the OCP/Col/PTH 0.1 μg/0.1 mL dropping group, and the OCP/Col/non-PTH administration group. The lower photographs show the results of the 3-TCP/Col/PTH 1.0 μg/0.1 mL dropping group, the β-TCP/Col/PTH 0.1 μg/0.1 ml dropping group, and the β-TCP/Col/non-PTH administration group. In the OCP/Col/PTH 1.0 μg/0.1 mL dropping group and the OCP/Col/PTH 0.1 μg/0.1 mL dropping group, radiopaque images were observed in large parts of the defects 4 weeks after implantation. The opacity of the images increased with time, and it was confirmed that the defects were recovered. On the other hand, in the OCP/Col group (non-PTH administration group), the entire defect was covered with an aggregate of scattered small radiopaque images 4 weeks after implantation. The images were fused while increasing their opacity with time, and the radiopaque images in the defect increased. This means that progression of opacity in the defect is slower in the non-PTH administration group than in the PTH administration group.

Figure 8:
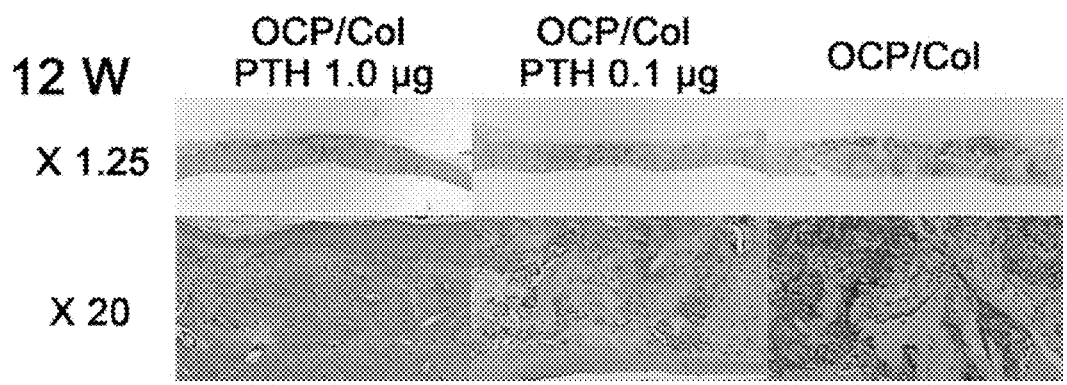
FIG. 8 shows the results of examining the influence of PTH dropped on bone defect sites treated with an OCP-containing porous composite, using stained pathological specimens. The upper side is the skin side, and the lower side is the endocranial side. The upper images are low-magnification (×1.25) images, and the lower images are high-magnification (×20) images.

FIG. 8 shows stained pathological specimens after implantation of 12 weeks. The upper side of each pathological specimen is the skin side, and the lower side is the endocranial side. In the OCP/Col/PTH 1.0 μg/0.1 mL dropping group and the OCP/Col/PTH 0.1 μg/0.1 mL dropping group of the low-magnification (×1.25) images (upper row), the inside of the defects was mostly filled with red-stained new bone, and the thickness of the new bone was maintained equal to that of the existing bone. There was no differentiated seam between the defect margins and the new bone. In the OCP/Col/PTH 1.0 μg/0.1 mL dropping group of the high-magnification (×20) image (lower row), most of the defect site was filled with new bone, which indicated positive bone modification, and part of the new bone was converted into cortical bone. Moreover, the implanted OCP granules were almost inconspicuous. In the OCP/Col/PTH 0.1 μg/0.1 mL dropping group, most of the defect site showed positive bone modification, and was filled with new bone integrated with the implanted OCP/Col, and part of the new bone was converted into cortical bone. Moreover, the implanted OCP granules were considerably smaller. The OCP/Col group showed a smaller amount of new bone than the OCP/Col/PTH dropping groups. The new bone integrated with the implanted OCP/Col had a mosaic form, and the implanted OCP granules were smaller.

Figure 9:
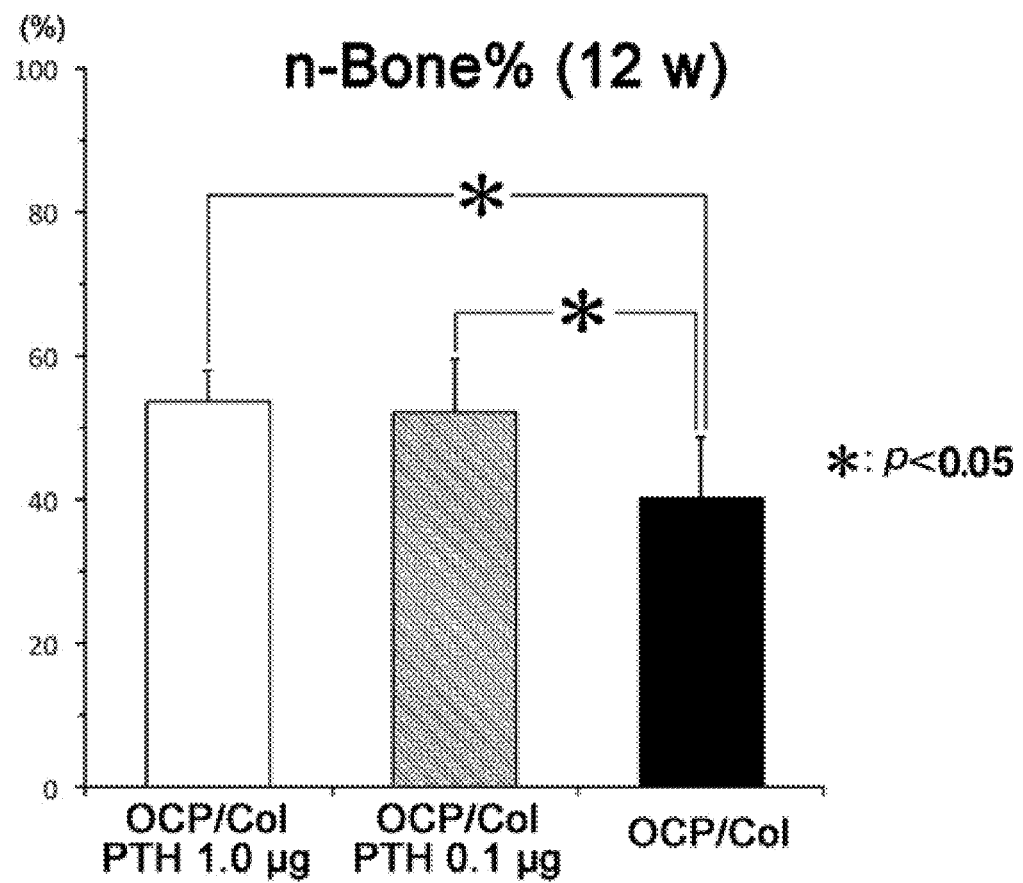
FIG. 9 shows the results of histomorphometric analysis of the influence of PTH dropped on bone defect sites treated with an OCP-containing porous composite.

FIG. 9 shows the measurement results of the histomorphometric analysis (ratio of new bone). The ratio of new bone (n-Bone %) in the defect was as follows: OCP/Col/PTH 1.0 μg/0.1 mL dropping group: 53.6±4.3, OCP/Col/PTH 0.1 μg/0.1 mL dropping group: 52.2±7.4, and OCP/Col group (non-PTH administration group): 40.1±8.4. It was confirmed that the combined use of PTH and OCP resulted in a significantly higher ratio of new bone than the single use of OCP (p=0.008).

As described above, the results shown in FIGS. 6 to 9 confirmed that new bone formation by OCP was significantly promoted by the combined use of PTH and OCP. In the subcutaneous injection group (10 μg/kg/day: 8 weeks) of Test Example 1, more than 150 μg of PTH was administered to the individual rats (body weight: about 250 to 350 g); however, it was confirmed that more excellent bone regeneration effects can be realized with a dosage of several hundredths to several thousandths of the above amount.

Test Example 3: OCP+FGF-2

Male Wistar rats (12 weeks old) were each intraperitoneally anesthetized, and a skin incision and a periosteal incision were made in the rat calvarium part to expose the calvarium. A standardized full-thickness bone defect (diameter: about 9 mm), for which spontaneous recovery could not be expected, was created. Then, the OCP/FGF-2 granules (15 mg) or OCP granules (15 mg) obtained in Production Example 6 were implanted therein. After the sample was implanted, the periosteum and skin were sutured, and the surgery was completed. Each group consisted of 4 or 5 rats, and was evaluated 4 weeks after surgery. Further, in the OCP/FGF-2 (100 ng) administration group and the OCP administration group (5 rats in each group), bone regeneration ability was examined 8 weeks after surgery.

After the observation period was over, the rats were euthanized under anesthesia with an excess amount of pentobarbital. The calvarium and surrounding tissue were taken, and immersed and fixed in 0.1 M phosphate-buffered 4% paraformaldehyde (pH 7.4). The extracted samples were photographed (20 kV, 5 mA) by a soft X-ray camera (CMBW-2, produced by Softex Co., Ltd.), and then decalcified with 10% EDTA to prepare paraffin samples. Then, tissue sections (thickness: 6 μM) cut in the frontal plane were prepared, and a histological search was performed by hematoxylin-eosin staining. Further, using the plural tissue sections corresponding to the center of the defect of each sample, the ratio of new bone (n-Bone %) in the created defect was examined by histological quantification. Variance analysis, etc., were conducted using the average value and standard deviation of n-Bone % in each group, and a significance test was conducted. The significance level was set at 5%.

Figure 10:
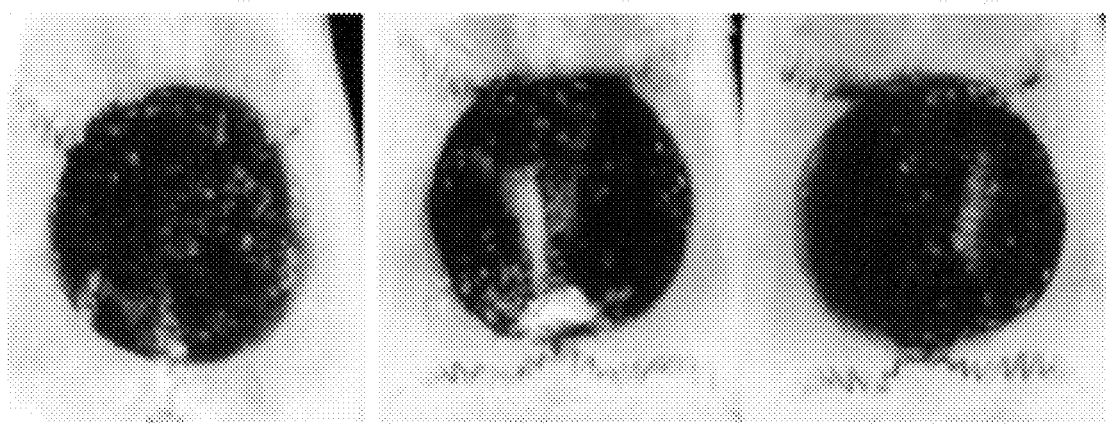
FIG. 10 shows the results of treating bone defect sites with OCP alone or a combination of OCP and FGF-2.
Figure 10:
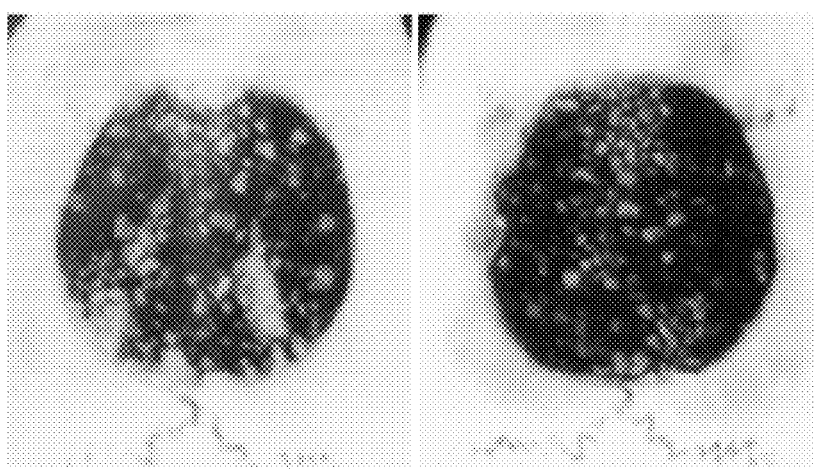

In the obtained soft X-ray photographs (FIG. 10), granular radiopaque images corresponding to the OCP/FGF-2 or OCP implanted in the defects were observed. Histologically, bone formation using the defect margins and the implanted OCP/FGF-2 or OCP as the core was observed in both the OCP/FGF-2 administration groups and the OCP administration group. In terms of histological quantification, the ratio of new bone (n-Bone %: average value±standard deviation) in the defect 4 weeks after surgery was as follows: 14.5±6.9% in the OCP/FGF-2 (10 ng) administration group, 16.7±19.3% in the OCP/FGF-2 (100 ng) administration group, and 9.7±3.9% in the OCP/FGF-2 (1 μg) administration group. There was no significant difference between these groups. Moreover, the ratio of new bone (n-Bone %: average value±standard deviation) in the defect 8 weeks after surgery was as follows: 12.8±5.8% in the OCP/FGF-2 (100 ng) administration group, and 10.4±10.4% in the OCP administration group. There was no significant difference between these groups. These results confirmed that the effect of promoting new bone formation by OCP was not obtained even by the combined use of OCP and FGF-2.

The invention claimed is:

1. A method of bone regeneration or bone augmentation, comprising:
   implanting a porous composite at a site in need of the bone regeneration or bone augmentation, and
   administering parathyroid hormone (PTH) to a subject in need of the bone regeneration or bone augmentation,
   wherein the porous composite comprises octacalcium phosphate (OCP) and collagen, and
   wherein the PTH is wild-type PTH or a derivative of wild-type PTH having the same physiological function as wild-type PTH.

2. The method of claim 1, wherein the porous composite is implanted, and then the PTH is administered.

3. The method of claim 2, wherein the PTH is administered topically to the site in need of the bone regeneration or bone augmentation.

4. The method of claim 3, wherein the PTH is administered topically to the site where the porous composite has been implanted.

5. The method of claim 1, wherein the PTH is administered subcutaneously.

6. The method of claim 1, wherein the PTH is administered to the subject, and then the porous composite is implanted.

7. The method of claim 6, wherein the PTH is administered topically to the site in need of the bone regeneration or bone augmentation.

8. The method of claim 6, wherein the PTH is administered subcutaneously.

9. The method of claim 1, wherein the site in need of the bone regeneration or bone augmentation is a site in need of the bone regeneration.

10. The method of claim 9, wherein the site in need of the bone regeneration is a site of bone defect.

11. The method of claim 1, wherein the site in need of the bone regeneration or bone augmentation is a site in need of the bone augmentation.

12. The method of claim 11, wherein the site in need of the bone augmentation is a site in need of at least one selected from the group consisting of sinus lift, bone graft, and ridge expansion.

13. The method of claim 1, wherein the PTH is teriparatide.

14. A method of bone regeneration or bone augmentation, comprising:

SEQUENCE LISTING

<160> NUMBER OF SEQ ID NOS: 1

<210> SEQ ID NO 1
<211> LENGTH: 34
<212> TYPE: PRT
<213> ORGANISM: Homo sapiens

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe implanting a porous composite at a site in need of the bone regeneration or bone augmentation, wherein the porous composite comprises octacalcium phosphate (OCP) and collagen and parathyroid hormone (PTH), and wherein the PTH is wild-type PTH or a derivative of wild-type PTH having the same physiological function as wild-type PTH.

15. The method of claim 14, wherein the site in need of the bone regeneration or bone augmentation is a site in need of the bone regeneration.

16. The method of claim 15, wherein the site in need of the bone regeneration is a site of bone defect.

17. The method of claim 14, wherein the site in need of the bone regeneration or bone augmentation is a site in need of the bone augmentation.

18. The method of claim 17, wherein the site in need of bone augmentation is a site in need of at least one selected from the group consisting of sinus lift, bone graft, and ridge expansion.

19. The method of claim 14, wherein the PTH is teriparatide.

* * * * *